United States Patent [19]

Habermeier

[11] 3,992,401

[45] Nov. 16, 1976

[54] BIS-(HYDANTOINYL)BENZIMIDAZOLENE COMPOUNDS CONTAINING HYDROXYALKYL GROUPS

[75] Inventor: Jurgen Habermeier, Pfeffingen, Switzerland

[73] Assignee: Ciba-Geigy Corporation, Ardsley, N.Y.

[22] Filed: July 8, 1975

[21] Appl. No.: 594,169

Related U.S. Application Data

[62] Division of Ser. No. 487,107, July 10, 1974, Pat. No. 3,928,377.

[30] Foreign Application Priority Data

July 30, 1973 Switzerland.................... 11053/73

[52] U.S. Cl. ............................................ 260/309.2
[51] Int. Cl.² ....................................... C07D 403/14
[58] Field of Search ................................ 260/309.2

[56] References Cited
UNITED STATES PATENTS

| | | | |
|---|---|---|---|
| 3,679,681 | 7/1972 | Habermeier et al. | 260/309.5 |
| 3,726,895 | 4/1973 | Habermeier et al. | 260/309.5 |
| 3,821,242 | 6/1974 | Habermeier et al. | 260/309.5 |
| 3,843,674 | 10/1974 | Porret | 260/309.5 |

OTHER PUBLICATIONS

Harrison et al., Chem. Abst., 1962, vol. 56, Cols. 12871–12872.

Derwent Abstract of Netherlands, 7311–7577, (20465v/11, Ciba–Geigy).

*Primary Examiner*—Natalie Trousof
*Attorney, Agent, or Firm*—Luther A. R. Hall

[57] ABSTRACT

New N-heterocyclic diols are obtained by an addition reaction of alkylene oxide with certain oligomeric compounds containing more than two hydantoin and/or benzimidazolone rings. The new diols are suitable for the manufacture of polyesters, polyurethanes, diacrylates and diglycidyl ethers, from which moulding materials having valuable thermomechanical properties can be manufactured.

3 Claims, No Drawings

BIS-(HYDANTOINYL)BENZIMIDAZOLENE COMPOUNDS CONTAINING HYDROXYALKYL GROUPS

This is a divisional of application Ser. No. 487,107 filed on July 10, 1974, now U.S. Pat. No. 3,928,377, issued Dec. 23, 1975.

The present invention relates to new di-(hydroxyalkyl) compounds of oligomeric N,N-heterocyclic structures and to a process for their manufacture.

German Offenlegungsschrift No. 1,954,503 describes the hydroxyalkylation of cyclic ureides, such as parabanic acid or barbituric acid, and N,N-heterocyclic compounds with a ureide structure, such as hydantoin or dihydrouracil, by an addition reaction of alkylene oxides with these compounds. Belgian Pat. Specification No. 744,846 also describes alkylene oxide addition products of compounds containing two N,N-heterocyclic rings.

It has now been found that an addition reaction of alkylene oxide with certain oligomeric compounds containing more than two N,N-heterocyclic rings gives, in good yields, the corresponding di-(hydroxyalkyl) compounds, which are new compounds and display, in comparison with the known di-(hydroxyalkyl) compounds of cyclic ureides, a more strongly heterocyclic character and, surprisingly, can be polycondensed with dicarboxylic acids to give polyesters having better thermo-mechanical properties.

The present invention relates to new di-(hydroxyalkyl) compounds of the general formula I

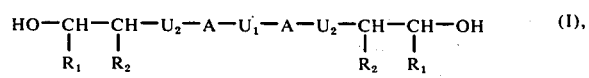

wherein $R_1$ denotes in each case a hydrogen atom or the methyl, ethyl or phenyl group, and $R_2$ denotes a hydrogen atom or, conjointly with $R_1$, denotes the tetramethylene radical, A denotes a radical of the formulae

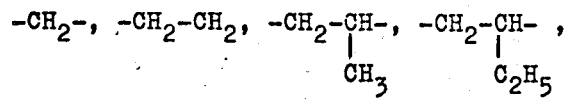

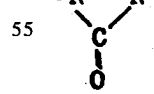

or

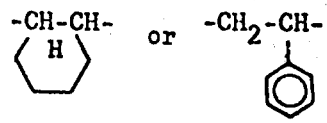

$U_1$ denotes a radical of the following formulae

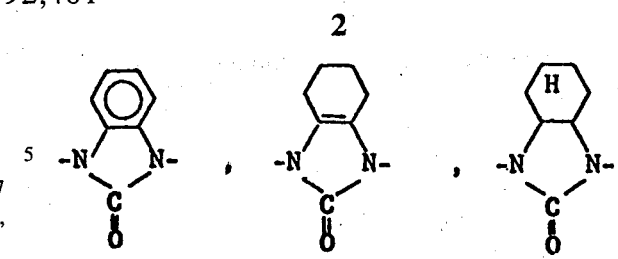

or

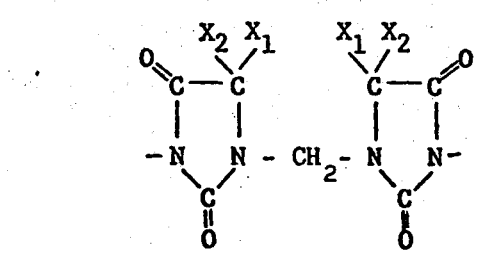

wherein $X_1$ and $X_2$ independently of one another each denote a hydrogen atom or an alkyl radical with 1 to 4 carbon atoms, and $U_2$ has the same meaning as $U_1$ or denotes a radical of the formula

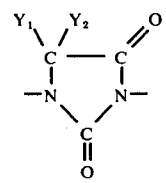

wherein $Y_1$ and $Y_2$ independently of one another each denote a hydrogen atom, an alkyl radical with 1 – 4 carbon atoms, or the phenyl group or conjointly denote the pentamethylene radical.

Preferably, in the Formula I, $R_1$ and $R_2$ each denote a hydrogen atom, A denotes the methylene or ethylene radical, $U_1$ denotes a radical of the formulae

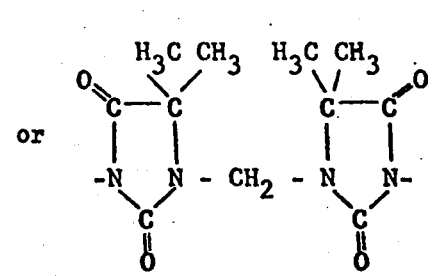

and $U_2$ denotes a radical of the formula

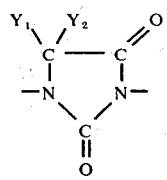

wherein $Y_1$ and $Y_2$ represent the methyl group or conjointly represnt the pentamethylene radical.

The new di-(hydroxyalkyl) compounds of the Formula I are obtained by an addition reaction, preferably in the presence of a catalyst, of two mols of an alkylene oxide of the formula III

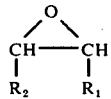 (III)

wherein $R_1$ and $R_2$ have the same meaning as in Formula I, with one mol of a compound of the formula II

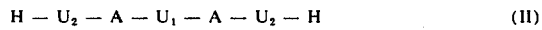 (II)

wherein A, $U_1$ and $U_2$ have the same meaning as in Formula I.

It is preferable to start from those compounds of the Formula II wherein A denotes the methylene or ethylene radical, $U_1$ denotes a radical of the formulae

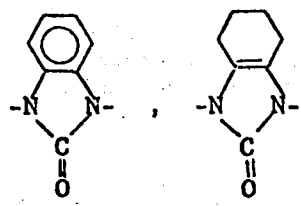

or

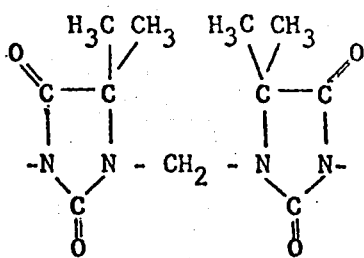

and $U_2$ denotes a radical of the formula

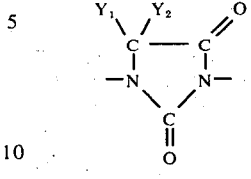

wherein $Y_1$ and $Y_2$ represent the methyl group or conjointly represent the pentamethylene radical, and to add on to those compounds an alkylene oxide, preferably ethylene oxide.

Compounds corresponding to the Formula III, apart from ethylene oxide, are propylene oxide, butylene oxide, styrene oxide and cyclohexene oxide.

The addition reaction of an alkylene oxide of the Formula III with the compound of Formula II, which contains two NH groups, can be carried out in the presence of either alkaline or neutral catalysts. This addition reaction also takes place without catalysts. The reaction temperature in this addition reaction is, as a rule, between 0° and 200° C; it is preferably raised, during the addition reaction, from about 15° C initially to about 120° C.

The addition reaction can also be carried out under pressure, that is to say in an autoclave. The addition reaction is preferably carried out in solution and dimethylacetamide, dimethylformamide, dioxane, halogenated hydrocarbons, water or mixtures of such solvents are preferentially used.

Suitable acid catalysts in the addition reaction are especially Lewis acids, such as, for example, $AlCl_3$, $SbCl_5$, $SnCl_4$, $FeCl_3$, $ZnCl_2$, $BF_3$ and complexes thereof with organic compounds.

Suitable catalysts with an alkaline action are above all tertiary amines, such as triethylamine, tri-n-propylamine, benzyldimethylamine, N,N'-dimethylaniline, and triethanolamine; quaternary ammonium bases, such as benzyltrimethylammonium hydroxide; quaternary ammonium salts, such as tetramethylammonium chloride, tetraethylammonium chloride, benzyltrimethylammonium chloride, benzyltrimethylammonium acetate and methyltriethylammonium chloride; and also ion exchange resins having tertiary or quaternary amino groups; and also trialkylhydrazonium salts, such as trimethylhydrazonium iodide.

The reaction can also be accelerated by the addition of other suitable catalysts, for example borax or alkali metal hydroxides, such as sodium hydroxide, and above all by the alkali metal halides which have a neutral reaction, such as lithium chloride, potassium chloride, sodium chloride, sodium bromide and sodium fluoride.

The compounds of the Formula II can be prepared either by reacting, with the elimination of 2 mols of hydrogen halide, 1 mol of a compound of the Formula IV

 (IV)

with 2 mols of a monohalogen compound of the Formula V

 (V)

wherein the expression "Hal" represents a halogen atom, or by reacting, with the elimination of 2 mols of hydrogen halide, 1 mol of a dihalogen compound of the Formula VI

    (VI)

with 2 mols of a compound of the Formula VII

    (VII)

These condensation reactions are, as a rule, carried out at elevated temperatures between 20° and 200° C, preferably between 50° and 140° C using in part a slowly rising temperature gradient between these values. The reactions are carried out in water or organic solvents, for example dioxane, dimethylformamide or dimethylacetamide. The hydrogen halide formed is either expelled at elevated temperatures by passing in nitrogen or, preferably however, is intercepted by neutralisation with corresponding bases. Examples of bases which can be used are NaOH, $K_2CO_3$, $Na_2CO_3$, triethylamine, pyridine or dimethylaniline.

The reaction mixture is worked up in the customary manner by separating from the solution the halide which is formed and by subsequent removal of the solvent by distillation. The products thus obtained can be purified by recrystallisation, rinsing or extraction.

Compounds corresponding to the Formula IV are, on the one hand, benzimidazolone, tetrahydrobenzimidazolone and hexahydrobenzimidazolone and, on the other hand, 1,1'-methylene-bis-(hydantoin) and its alkyl-substituted derivatives, such as, for example, 1,1'-methylene-bis-(5,5-dimethylhydantoin), 1,1'-methylene-bis-(5-methyl-5-ethylhydantoin), 1,1'-methylene-bis-(5-propylhydantoin) and 1,1'-methylene-bis-(5-isopropylhydantoin).

In addition to compounds of the Formula IV, the Formula VII also includes hydantoin and its alkyl-, phenyl- and cyclohexyl-substituted derivatives, such as, for example, 5-methylhydantoin, 5,5-dimethylhydantoin, 5-methyl-5-ethylhydantoin, 5-isopropylhydantoin, 5-phenylhydantoin and 5,5-pentamethylenehydantoin (1,3-diaza-spiro(4,5)-decane-2,4-dione).

Examples which may be mentioned of suitable monohalogen compounds of the Formula V are the halogenoalkyl-substituted hydantoin derivatives such as 3-chloromethyl-5,5-dimethylhydantoin, 3-chloromethyl-5,5-pentamethylenehydantoin, 3-bromomethyl-5,5-dimethylhydantoin, 3-(β-chloroethyl)-5,5-dimethylhydantoin, 3-(β-chloroethyl)-5-methyl-5-ethylhydantoin, 3-(B-chloro-β-chlorocyclohexyl)-5,5-dimethylhydantoin and 3-(β-phenylethyl)-5-isopropylhydantoin.

These monohalogen compounds can be prepared by known methods by reacting the corresponding known monohydroxyalkylhydantoins with compounds which introduce chlorine or bromine, especially with acid halides, preferably inorganic acid halides, such as $SOCl_2$ or $SOBr_2$.

The dihalogen compounds of the Formula VI can be prepared, on the one hand, analogously to the monohalogen compounds of the Formula V, by reacting the corresponding known dihydroxyalkyl compounds with compounds which introduce chlorine or bromine, or, on the other hand, by reacting the 3-(β-halogenoalkyl) compounds of the Formula V with formaldehyde according to the process described in U.S. Pat. Nos. 2,404,096 and 2,417,999.

The following may be mentioned as suitable compounds of the Formula VI: 1,1'-methylene-bis-(3-β-chloroethyl-5,5-dimethylhydantoin), 1,1'-methylene-bis-(3-β-bromoethyl-5,5-diethylhydantoin), 1,1'-methylene-bis-(3-β-chloro-n-propyl-5,5-dimethylhydantoin), 1,1'-methylene-bis-(3-β-chloro-n-propyl-5-isopropylhydantoin), 1,1'-methylene-bis-(3-β-bromo-butyl-5,5-dimethylhydantoin), 1,1'-methylene-bis-(3-β-chlorocyclohexyl-5,5-dimethylhydantoin) and 1,1'-methylene-bis-(3-β-chloro-β-phenylethyl-5-isopropylhydantoin) as well as 1,3-bis-(β-chloroethyl)-benzimidazolone, 1,3-bis(β-chloro-n-propyl)-benzimidazolone, 1,3-bis-(β-bromo-β-phenylethyl)-benzimidazolone, 1,3-bis-(β-bromo-n-propyl)5-methyl-benzimidazolone, 1,3-bis-(chloromethyl)-benzimidazolone, 1,3-bis-(β-chloroethyl)-tetrahydrobenzimidazolone, 1,3-bis-(β-bromo-n-propyl)-tetrahydrobenzimidazolone, 1,3-bis-(β-chloro-β-phenylethyl)-tetrahydrobenzimidazolone and 1,3-bis-(β-chloroethyl)-hexahydrobenzimidazolone.

Some of the new di-(hydroxyalkyl) compounds of the Formula I can also be obtained, with elimination of hydrogen halide, by reacting certain compounds of the Formula II, in which the terminal N,N-heterocyclic rings contain free 3-NH groups, with a monohalogenomonohydroxyalkane having 2–4 carbon atoms in the molecule, preferably with the 1-chloro-2-hydroxyalkanes.

In the purified state, the new di-(hydroxyalkyl) compounds are colourless, crystalline powders with melting points between 40° C and 250° C. The diols are readily soluble in solvents such as dimethylformamide, dioxane, acetone, ethanol and methanol and, for the most part, also in water.

The di-(hydroxyalkyl) compounds according to the invention can be converted, by reaction with, for example, polycarboxylic acids or alkyl esters or halides thereof, into polyesters, or, by reaction with polyisocyanates, into polyurethanes, having very valuable mechanical properties from a technical point of view.

The di-(hydroxyalkyl) compounds according to the invention can also be converted, by reaction with epihalogenohydrin, into the corresponding diglycidyl ethers, or, by esterification with acrylic acid or methacrylic acid, into the corresponding diacrylates, which are valuable resins and which can be processed into plastics having valuable mechanical properties.

Preparation of the starting substances

Example A

Tetrahydantoin compound from 1 mol of 1,1'-methylene-bis-(5,5-dimethylhydantoin) and 2 mols of 3-chloromethyl-5,5-dimethylhydantoin.

A mixture of 134.1 g of 1,1'-methylene-bis-(5,5-dimethylhydantoin) (0.5 mol) and 193 g of 3-chloromethyl-5,5-dimethylhydantoin (1.05 mols) is ground in a mortar to a fine, homogeneous powder and is then poured into a laboratory stirring apparatus made of glass. 75.9 g of finely ground potassium carbonate (0.55 mol) and 800 ml of N,N-dimethylacetamide (DMA) are added to the mixture. The suspension thus formed is intensively stirred at an internal temperature of 60° C. After 1 hour at 60° C, stirring is continued for 2 hours at 80° C and for a further 2 hours at 100° C. The solution is then filtered hot in order to remove potassium chloride and residues of potassium carbonate. The clear, faintly coloured solution is concentrated to dryness at 80° C and is then dried to constant weight at 80° C under 0.4 mm Hg pressure.

275 g of the crude tetrahydantoin compound are obtained as a light-brown, brittle, resinous substance.

The substance is purified by recrystallisation from dimethylformamide/isopropanol (mixing ratio 4:1). 240 g (87.4% of the theoretical yield) are obtained of a colourless powder melting at 284.1° C ("Mettler FP 51"; rate of heating 2° C/minute).

Elementary analysis indicates:

| Found: | Calculated: |
|---|---|
| 50.6% C | 50.4% C |
| 6.1% H | 5.9% H |
| 20.0% N | 20.4% N. |

The product can be further purified by recrystallisation from methanol. In this way very fine, colourless, fibre-shaped crystals are obtained, melting at 286.5° – 287° C ("Mettler FP 51"; rate of heating 1° C/minute).

Elementary analysis indicates:

| Found: | Calculated: |
|---|---|
| 50.26% C | 50.36% C |
| 5.88% H | 5.88% H |
| 20.31% N | 20.43% N. |

Only 1 spot of substance appears in a thin layer chromatogram (TLC) (migrating agent: a solvent mixture composed of cyclohexane, ethyl acetate and acetic acid in a mixing ratio of 30:50:20); the $R_f$ value = 0.23. The mass spectrum indicates, through the molecule ion at 548 mass units and through characteristic fragment ions, that the desired tetrahydantoin compound has been formed. The proton-magnetic resonance spectrum (100 megacycles; recorded in a mixture of $CDCl_3$ and completely deuterated dimethylsulphoxide) shows, by the presence of the corresponding signals, that the tetrahydantoin compound has the following structure:

Example B

Tetrahydantoin compound from 1 mol of 1,1'-methylene-bis-(5,5-dimethylhydantoin) and 2 mols of 3-(2'-chloroethyl)-5,5-dimethylhydantoin.

A mixture of 339.3 g of 1,1'-methylene-bis-(5,5-dimethylhydantoin) (1.264 mols), 570 g of 93% strength 3-(2'-chloroethyl)-5,5-dimethylhydantoin (2.78 mols), 192.1 g of finely powdered potassium carbonate and 1,270 ml of dimethylformamide (DMF) is stirred for 2 hours at 120° C, the reaction taking place with a vigorous evolution of $CO_2$. The reaction mixture is then stirred for a further 4 hours at 130° C. After cooling, the reaction product is worked up is accordance with Example A and 811 g are obtained of a colourless, solid, glassy substance, which still contains some DMF. (theoretical yield = 728.8 g).

This crude product is recrystallised from 50% strength ethanol (ratio of substance: solvent: 1 : 3.5). 508.2 g of a fine, colourless crystalline product are obtained (69.7% of the theoretical yield), the melting point of which is 261.0° C. The elementary analysis for the tetrahydantoin compound ($C_{25}H_{36}N_8O_8$) indicates:

| Found: | Calculated: |
|---|---|
| 51.8% C | 52.1% C |
| 6.4% H | 6.3% H |
| 19.4% N | 19.4% N. |

The proton-magnetic resonance spectrum (60 megacycles) shows, by signals at $\delta = 1.32 + 1.48; 3.70; 5.00; 7.80$ with an intensity ratio of 24 : 8 : 2 : 2, that the tetrahydantoin compound has the following structure:

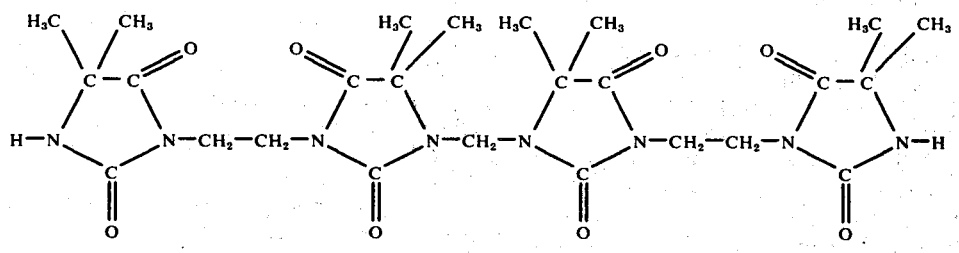

EXAMPLE C

Tetrahydantoin compound from 2 mols of 3-chloroethyl-5,5-pentamethylenehydantoin and 1 mol of 1,1'-methylene-bis-(5,5-dimethylhydantoin).

A mixture, in 600 ml of dimethylformamide, of the following substances: 115.3 g of 3-(2'-chloroethyl)-5,5-pentamethylenehyandtoin (0.5 mol), 67.5 g of 1,1'-methylene-bis-(5,5-dimethylhydantoin) (0.25

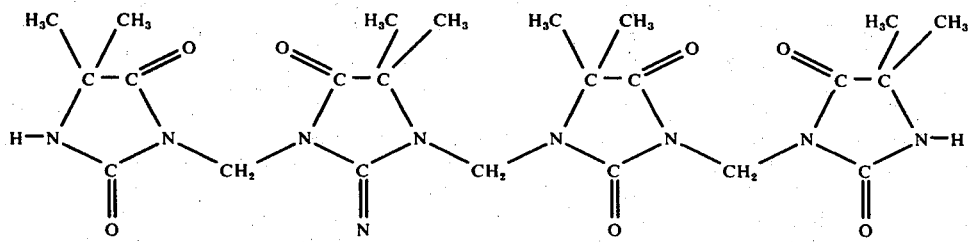

mol) and 40.7 g of finely powdered potassium carbonate (0.3 mol) is stirred for 8 hours at 120° – 130° C.

The mixture is worked up in accordance with Example A, after the solution has, in addition, previously been filtered, while at 100° C.

172.8 g (theoretical yield: 164.2 g) are obtained of an ochre-coloured, crystalline powder, melting at 283° – 286° C.

This crude product is purified by extraction with isopropanol, by stirring the finely powdered substance for 2 hours in 500 ml of boiling isopropanol and then cooling and filtering, and drying the residue to constant weight at 90° C/40 mm Hg.

146.3 g (89.1% of the theoretical yield) are obtained of a crystalline product with a pale ochre colour, which melts at 290° – 292° C. The elementary analysis for $C_{31}H_{44}N_8O_8$ indicates:

The crude product is purified by recrystallising twice from dimethylformamide (substance: solvent = 1:2). 428 g of a colourless crystalline product (66% of theory) which has a melting point of 242° – 243° C, are thus obtained.

The elementary analysis for $C_{21}H_{26}N_6O_5$ indicates:

| Found: | Calculated: |
|---|---|
| 57.10% C | 57.01% C |
| 5.88% H | 5.92% H |
| 19.10% N | 19.00% N. |

The new compound corresponds to the following formula:

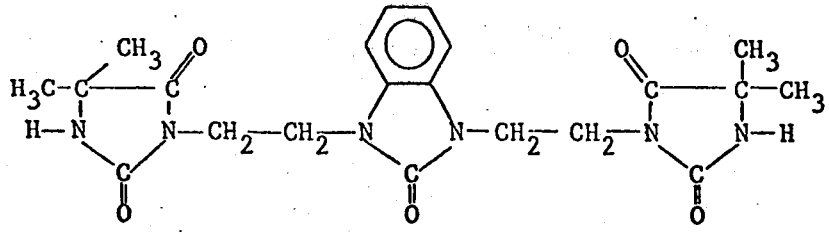

| Found: | Calculated: |
|---|---|
| 56.70% C | 56.70% C |
| 6.90% H | 6.75% H |
| 17.00 N | 17.06% N. |

The thin layer chromatogram indicates that the product is a single substance. The new tetrahydantoin compound corresponds to the following structure:

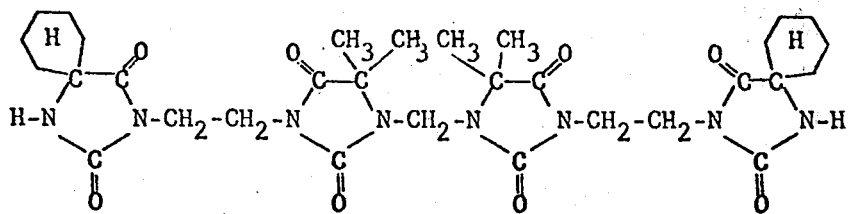

EXAMPLE D

Bis-(hydantoinyl)-benzimidazolone compound from 1,3-dichloroethylbenzimidazolone and 5,5-dimethylhydantoin.

A mixture of 380.0 g of 1,3-di-(2'-chloroethyl)-benzimidazolone (1.466 mols), 375.7 g of 5,5-dimethylhydantoin (2.93 mols) and 223 g of potassium carbonate (anhydrous and ground; 1,61 mols) in 4.4 liters of dimethylformamide is stirred for 2 hours at 120° C and for 3 hours at 130° C. The reaction mixture is then cooled to 90° C and filtered and the filtrate is concentrated to dryness. The residue is dried to constant weight at 120° C/0.5 mm Hg and 648.5 g (100% of theory) of crude product melting at 214.5° C are obtained.

EXAMPLE E

Tetrahydantoin compound from 2 mols of 5,5-pentamethylenehydantoin and 1 mol of 1,1'-methylene-bis-[3-(2'-chloroethyl)-5-ethyl-5-methylhydantoin].

The following mixture of substances in 500 ml of dimethylformamide is reacted in accordance with Example C: 84.3 g of 1,1'-methylene-bis-[3-(2'-chloroethyl)-5-ethyl-5-methylhydantoin] (0.2 mol), 67.2 g of 5,5-pentamethylenehydantoin (0.4 mol) and 33.2 g of anhydrous, ground potassium carbonate (0.24 mol).

This mixture is stirred for 3 hours at 120° C and for 6 hours at 130° C. The new tetrahydantoin is worked up and purified by the procedure described in Example C. Yield of crude product: 141 g (theory 136 g). Yield of purified substance: 74.3 g (53.8% of theory). Melting point 257° – 259° C.

The elementary analysis for $C_{33}H_{48}N_8O_8$ indicates:

| Found: | Calculated: |
|---|---|
| 57.6% C | 57.88% C |
| 7.3% H | 7.01% H |
| 16.0% N | 16.36% N |

Preparation examples

EXAMPLE 1

Preparation of a diol from the tetrahydantoin compound of Example B.

503.7 g (0.874 mol) of the tetrahydantoin compound prepared in accordance with Example B and 3 g of lithium chloride in 1,050 ml of dimethylformamide are warmed to 50° C with stirring. A solution of 92.5 g (2.098 mols) of ethylene oxide in 525 ml of dimethylformamide is added dropwise to this suspension over the course of 2 hours. The temperature is then raised to 100° C over the course of 3 hours, a clear, colourless solution being formed. After a further 4 hours at 100° C, the solution is cooled to room temperature, neutralised (to universal indicator paper) with 50% strength aqueous sulphuric acid and concentrated to dryness and the residue is then dried to constant weight at 120° C/0.4 mm Hg.

A light-brown, clear, glassy-brittle product is obtained in practically quantitative yield: 581.4 g (theory: 581 g).

The product is purified by recrystallisation from 1,150 ml of ethyl acetate. A colourless, free-flowing, fine crystalline product, melting at 166°–168° C, is obtained in a 64.6% yield of pure product (375 g). The gel permeation chromatogram indicates, through the presence of a single spot, the $R_f$ value of which at 0.09 is not identical with that of the starting material, that a single, pure substance has been obtained. Elementary analysis indicates:

| Found: | Calculated: |
|---|---|
| 52.40% C | 52.40% C |
| 6.70% H | 6.67% H |
| 16.90% N | 16.86% N. |

The proton-magnetic resonance spectrum accords with the structure which follows, as also does the mass spectrum, which indicates the molecule ion at 664 (theoretical molecular weight: 664.7) and contains characteristic fragment ions:

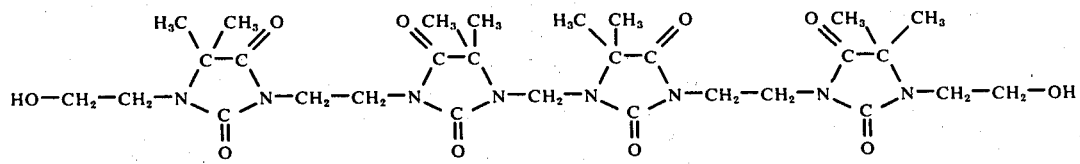

EXAMPLE 2

Preparation of a diol from the tetrahydantoin compound of Example C.

65.7 g (0.1 mol) of the tetrahydantoin compound prepared in accordance with Example C are introduced into a steel autoclave holding 200 ml, together with 0.5 g of lithium chloride and 50 ml of dimethylacetamide. 13.2 g of ethylene oxide (0.3 mol) in 50 ml of dimethylacetamide are then added and the mixture is heated, with stirring, for 5 hours at 150° C. The initial pressure of 5 atmospheres falls away to normal pressure over the course of approximately 1 hour. After the completion of the reaction, the solution is cooled to room temperature and the pH is adjusted to 7.0 with 20% strength sulphuric acid and a small quantity of undissolved matter is filtered off. The clear solution is concentrated completely at 140° C and the residue is dried to constant weight at 140° C under 0.3 mm Hg pressure. 77 g are obtained of a light-brown, solid substance (which still contains residues of dimethylacetamide) softening at 104° C (by Kofler's method).

This diol can be further purified by reprecipitation and extraction. The pure substance corresponds to the following structure:

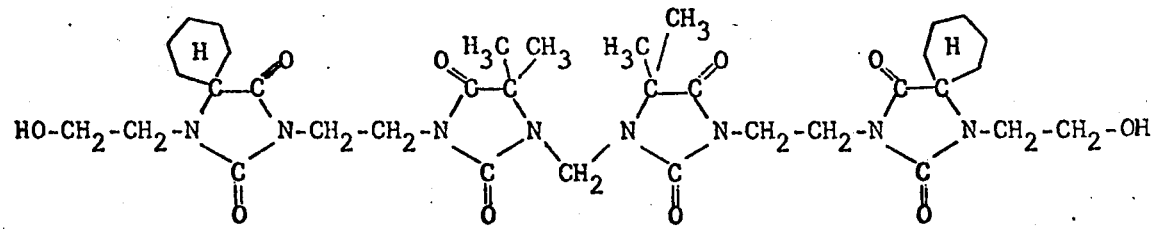

EXAMPLE 3

Preparation of a diol from the tetrahydantoin compound of Example A.

550.6 g (1.0 mol) of the tetrahydantoin compound prepared in accordance with Example A are stirred at 50° C with 3.2 g of lithium chloride and 1,200 ml of dimethylacetamide. A solution of 106 g of ethylene oxide (2.4 mols) in 600 ml of dimethylacetamide is added dropwise to this suspension over the course of 1 hour, a clear, yellow solution being formed. The temperature of the reaction mixture is raised from 50° C to 100° C over the course of 2 hours. The mixture is then stirred for a further 5 hours at 100° C. After cooling to room temperature, the reaction mixture is neutralised with a few drops of 20% strength sulphuric acid, filtered and concentrated completely at 120° C and is treated for 2 hours at 120° C under 0.3 mm Hg pressure. 717.8 g (theory: 638.7 g) are obtained of a clear, light brown, resinous product which still contains dimethylacetamide.

This is purified by dissolving in 750 ml of acetone and precipitating by stirring the solution into 5 liters of ether/petroleum ether (mixing ratio 1:1). The precipitated product is a colourless, resinous mass, which, after decanting off the mixture of solvent and precipitant, is dissolved in fresh acetone. This solution is boiled up with 10 g of active charcoal for 10 minutes, filtered to give a clear solution and concentrated completely at 50° C.

The product is then dried at 50° C/0.2 mm Hg. The resulting colourless, crystalline mass is finally pulverised and dried to constant weight in a dessicator over $P_2O_5$.

Colourless crystals melting at 78° C are obtained ("Mettler FP 51"; rate of heating 2° C/minute). The elementary analysis gives the following result:

| Found: | Calculated: |
|---|---|
| 50.57% C | 50.94% C |
| 6.82% H | 6.33% H |
| 17.66% N | 17.60% N. |

The new diol corresponds to the following structure:

The product obtained is then dried to constant weight at 100° C/0.5 mm Hg. 357 g of a glassy mass (100% of theory) are obtained.

This crude product is purified by dissolving in 1 l of acetone; the solution is filtered and 5 l of diethyl ether are added to the filtrate. The solvent/precipitant mixture is separated from the precipitated product by decantation. The product is taken up in 1 l of acetone and the solution is concentrated to dryness. The product, melting at 59° C, obtained in this way in a 78.7% yield (281.1 g) can be further purified by recrystallisation from acetone, with the aid of active charcoal.

This gives 216 g of a practically colourless product melting at 80° – 81° C.

The elementary analysis for $C_{25}H_{34}N_6O_7$ gives:

| Found: | Calculated: |
|---|---|
| 56.2% C | 56.58% C |
| 6.5% H | 6.46% H |
| 15.5% N | 15.83% N. |

The new diol accordingly has the following structure:

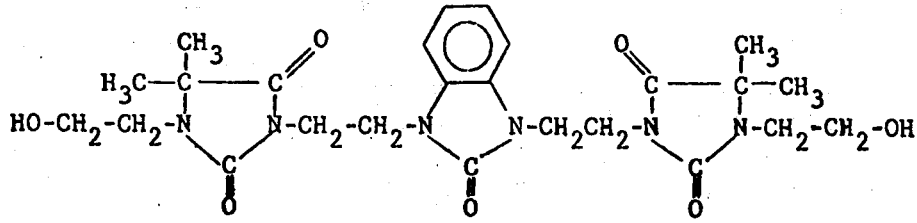

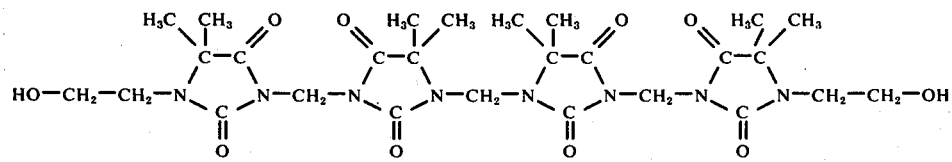

EXAMPLE 4

Preparation of a diol from the bis-(hydantoinyl)-benzimidazolone compound of Example D.

A solution of 95 g (2.16 mols) of ethylene oxide in 350 ml of dimethylformamide is added, at room temperature and with stirring, to a suspension of 298 g (0.673 mol) of the compound containing three N-heterocyclic rings, prepared in accordance with Example D, and 6.5 g of lithium chloride in 2 l of dimethylformamide. The mixture is warmed to 50° C while stirring and is kept at this temperature for 120 minutes. The mixture is then brought to a reaction temperature of 100° C over the course of 2 hours and is stirred for 5 hours at this temperature. After cooling, the reaction mixture is neutralised with a few ml of 20% strength sulphuric acid, filtered and concentrated to dryness.

EXAMPLE 5

Preparation of the diol from the tetrahydantoin of Example E 51.3 g (0.075 mol) of the tetrahydantoin prepared according to Example E, 60 ml of dimethylacetamide, 0.7 g of lithium chloride and 9.9 g of ethylene oxide are reacted in an autoclave holding 200 ml under the conditions described in Example 2. The diol formed is also worked up and purified in accordance with Example 2.

57.8 g of crude product (99% of theory) with a softening point of 100° C (Kofler) are obtained. 45.7 g of pure product are obtained; the melting point of the pure substance is 96° – 98° C.

According to the H-NMR spectrum (in $CDCl_3$), the structure of the new diol accords with the following formula:

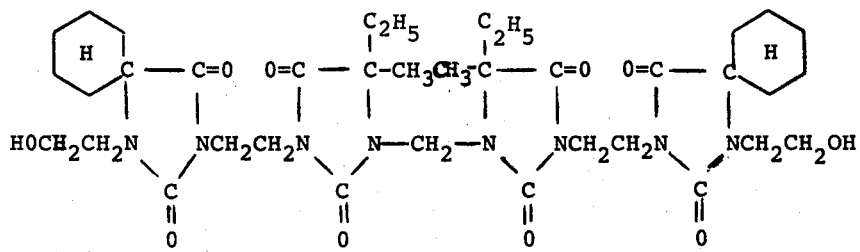

Application examples

EXAMPLE I

Preparation of a copolyester from the diol prepared in accordance with Example 3, butanediol and dimethyl terephthalate A mixture of 75 g of dimethyl terephthalate (DMT) (0.386 mol), 70 g of 1,4-butanediol (0.777 mol), 24.6 g of the diol of Example 3 (10 mol % relative to DMT) and 0.045 g of tetraisopropyl orthotitanate is condensed under an atmosphere of nitrogen and with slow stirring according to the following temperature/pressure programme:

1 hour at 160° C/$N_2$/atmospheric pressure,
2 hours at 160° C 245° C/$N_2$/atmospheric pressure,
1 hour at 245° C/$N_2$/atmospheric pressure 18 mm Hg,
30 minutes at 245° C/$N_2$/18 mm Hg 0.5 mm Hg and
1 hour at 265° C/$N_2$/0.5 mm Hg.

The reaction product is then poured out under a $N_2$-atmosphere to cool on a sheet of metal.

The practically colourless, partly crystalline copolyester thus obtained has the following values:

| | |
|---|---|
| Softening point (by Kofler's method) | : 207° C |
| Nitrogen content, measured | : 3.85% (theory 4.0) |
| Relative viscosity (at 30° C, 1% strength solution in a 1:1 mixture of phenol/tetrachloroethane) | : 1.62 |
| Glass transition range | : 104–111° C |
| Glass transition range | : 72–97° C |
| Glass transition point | : 95° C. |

Comparison example:

An analogous mixture which, however, contains 20 mol % of 1,1'-methylene-bis-[3-(2'-hydroxyethyl)-5,5-dimethylhydantoin] instead of 10 mol % of the diol of Example 3, is condensed under the conditions indicated in Example I. A copolyester is obtained in this way, which contains almost the same proportion by weight of dimethylhydantoin radicals in comparison with the copolyester according in Example I, and which has the following properties.

The following table quotes, in addition, the data of a commercially available polybutylene terephthalate:

| | Copolyester according to Example I | Copolyester according to the Comparison Example | Polybutyleneterephthalate |
|---|---|---|---|
| Softening point (Kofler's method) ° C | 207 | approx. 185 | 223 |
| Relative viscosity | 1.62 | 1.70 | 2.2 |
| c = partly crystalline | c | c | c |
| a = amorphous | | | |
| Glass transition temperature ° C | 95 | 59 | 24 |

If only 10 mol % instead of 20 mol % of the diol used in the comparison example are used, a copolyester with a glass transition temperature of only 45° C is obtained.

Example II

Preparation of the diglycidyl ether from the diol prepared in accordance with Example 5.

38.6 g (0.05 mol) of the diol prepared in accordance with Example 5 are dissolved at 90° C in 138.9 g (1.5 mols) of epichlorohydrin with the addition of 0.35 g of 50% strength aqueous tetramethylammonium chloride solution and the mixture is stirred at this temperature for 1 hour. By applying a vacuum, an azeotropic recycling distillation is then set in progress in such a way that, with vigorous stirring of the reaction mixture and maximum recycle of epichlorohydrin, a reaction temperature of 51° – 61° C is maintained. 9.6% strength aqueous sodium hydroxide solution is then added dropwise over the course of 1½ hours. The water formed in the reaction and the water acting as solvent for the sodium hydroxide solution and the catalyst is continuously removed from the batch by azeotropic distillation and is discarded. Distillation is continued for 5 minutes more after the addition of the sodium hydroxide solution and the reaction solution is then cooled to 40° C and the vacuum is released and the mixture is then filtered by suction to give a clear solution. The filtrate is shaken with twice 100 ml of water and the epichlorohydrin solution is then separated and concentrated to dryness on a rotary evaporator at a bath temperature of 60° C under a water pump vacuum. The residue is then dried to constant weight for a further 2 hours at 70° C/0.3 mm Hg.

31.6 g (81.6% of theory) of a clear, yellowish, solid resin are obtained, which has a softening point (by Kofler's method) of 65° C. The epoxide group content of the new epoxide resin is 2.0 equivalent/kg (88.8% of theory). According to analytical data, the product obtained corresponds to the following structure:

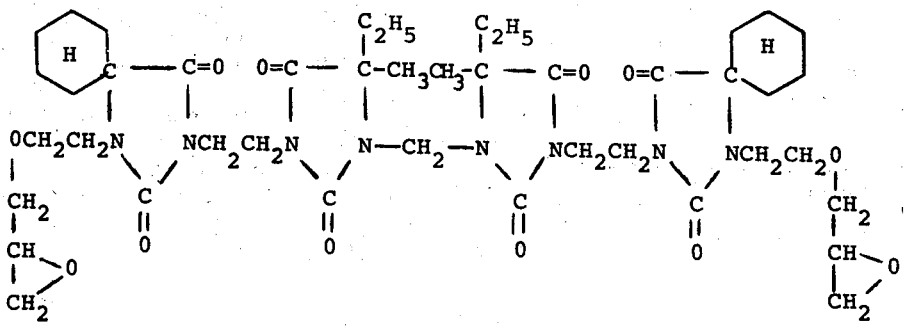

I claim:

1. A di-(hydroxyalkyl) compound of the formula

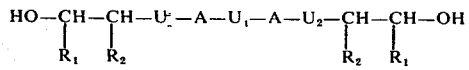

wherein each $R_1$ denotes a member selected from the group consisting of hydrogen, methyl, ethyl and phenyl, R₂ denotes hydrogen or together with R₁ denotes tetramethylene, A denotes a member selected from the group consisting of a divalent residue of the formulae

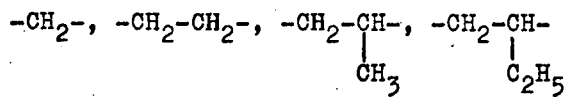

U₁ denotes a divalent residue of the formula

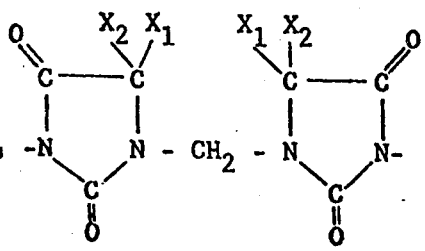

and U₂ denotes wherein X₁ and X₂ each denotes hydrogen or an alkyl with 1 to 4 carbon atoms or denotes a residue of the formula

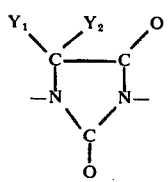

wherein Y₁ and Y₂ each denotes hydrogen, an alkyl with 1–4 carbon atoms or phenyl or together denote pentamethylene.

2. A di-(hydroxyalkyl) compound according to claim 1, wherein in the formula R₁ and R₂ each denotes hydrogen, A denotes methylene or ethylene, U₁ denotes a divalent residue of the formula

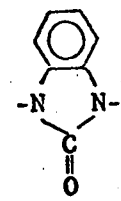

and U₂ denotes a residue of the formula

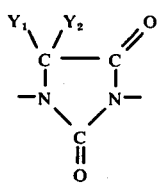

wherein Y₁ and Y₂ each represents methyl or together represent pentamethylene.

3. Di-(hydroxyethyl) compound according to claim 1 of the formula

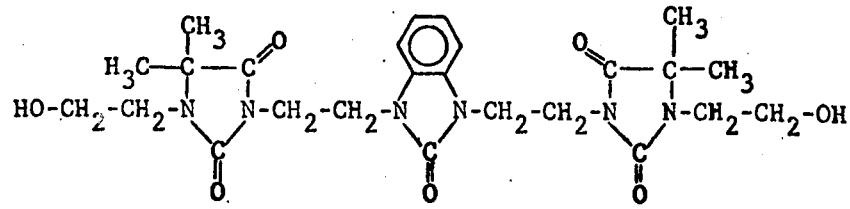

* * * * *